United States Patent [19]
Carenzo et al.

[11] Patent Number: 5,136,202
[45] Date of Patent: Aug. 4, 1992

[54] MATERIAL SENSOR

[75] Inventors: Anthony Carenzo, Audubon; Mary D. Kehrhahn, Paoli, both of Pa.

[73] Assignee: Atochem North America, Inc, Philadelphia, Pa.

[21] Appl. No.: 576,693

[22] Filed: Aug. 31, 1990

[51] Int. Cl.$^5$ .................................. H01L 41/08
[52] U.S. Cl. .................... 310/330; 310/319; 310/323; 310/800
[58] Field of Search ............. 310/330–332, 310/319, 323, 365, 800

[56] References Cited

U.S. PATENT DOCUMENTS

| | | | |
|---|---|---|---|
| T932,003 | 3/1975 | Strawser | 340/259 |
| 2,578,620 | 12/1951 | Wilhelm | 310/328 |
| 3,467,149 | 9/1969 | Dosch et al. | 310/323 X |
| 3,880,001 | 4/1975 | Hogan | 73/160 |
| 4,110,654 | 8/1978 | Paul | 310/323 |
| 4,311,958 | 1/1982 | Aeppli | 324/61 |
| 4,361,777 | 11/1982 | Mettler | 310/330 |
| 4,443,730 | 4/1984 | Kitamura et al. | 310/800 |
| 4,538,139 | 8/1985 | Clemente | 310/330 X |
| 4,605,875 | 8/1986 | Bobbola | 310/330 |
| 4,633,122 | 12/1986 | Radice | 310/365 X |
| 4,638,468 | 1/1987 | Francis | 310/800 X |
| 4,734,044 | 3/1988 | Radice | 310/365 X |
| 4,768,026 | 8/1988 | Makino | 340/677 |
| 4,883,531 | 11/1989 | Cole et al. | 73/9 |

OTHER PUBLICATIONS

*Kynar® Piezo Film Technical Manual*, (1987), Pennwalt Corporation, Philadelphia, Pa.
"*Kynar® Piezo Film Product Summary and Price List*" (1988) Pennwalt Corporation, Philadelphia, Pa.

*Primary Examiner*—Mark O. Budd
*Attorney, Agent, or Firm*—Woodcock Washburn Kurtz Mackiewicz & Norris

[57] ABSTRACT

A material sensor employs deflectable means and piezoelectric film means for providing signals indicative of a material condition.

42 Claims, 5 Drawing Sheets

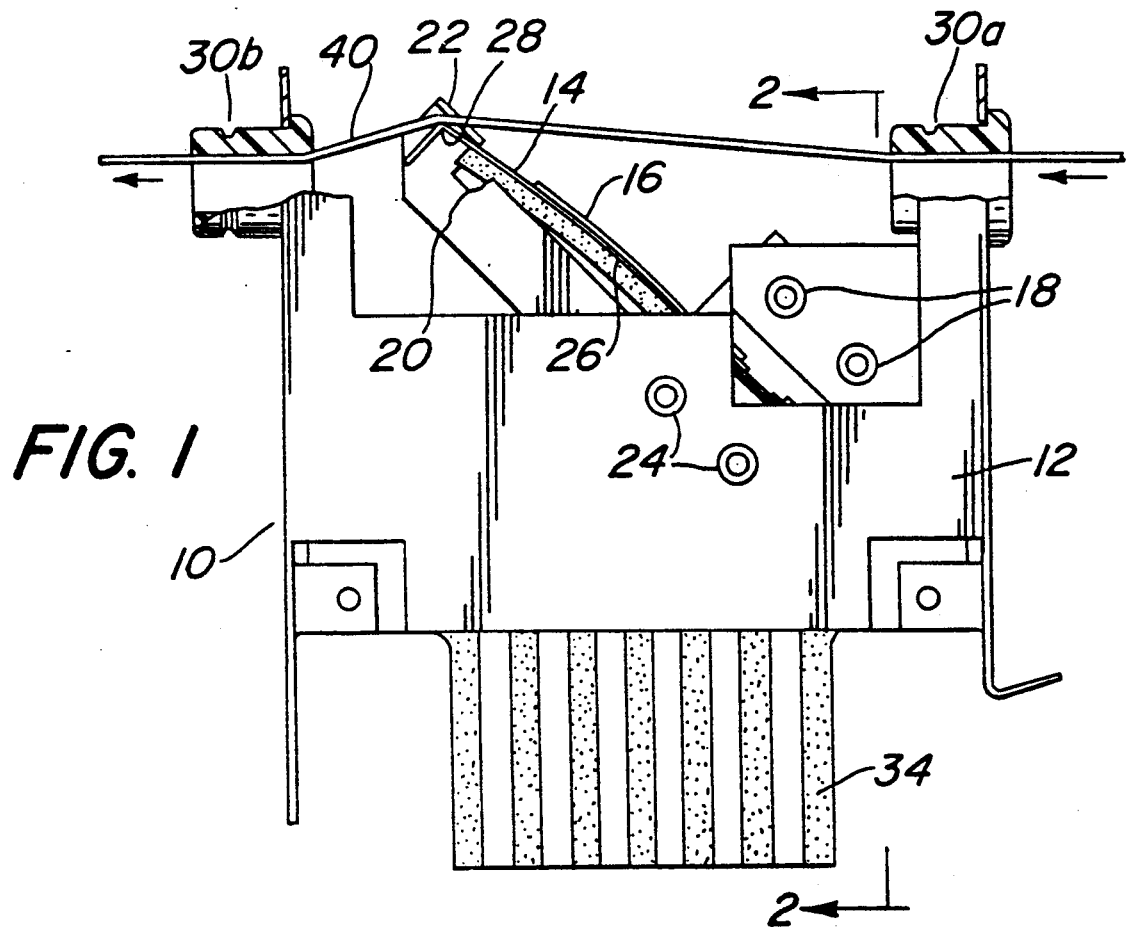
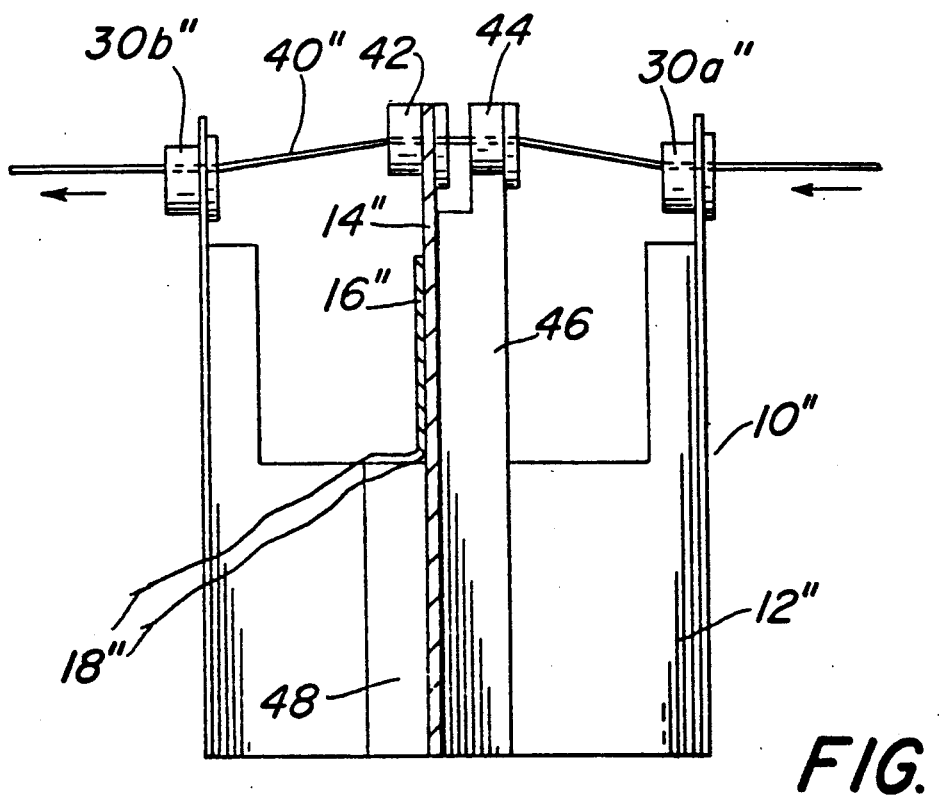

MATERIAL SENSOR

FIELD OF THE INVENTION

The present invention relates generally to apparatus for sensing tension and detecting breakage of a continuous material, such as filaments or thread. Specifically, the present invention relates to apparatus for sensing thread tension and detecting thread breakage during processes involving either synthetic or natural threads. More specifically, the present invention relates to apparatus employing piezoelectric film for such purposes.

BACKGROUND OF THE INVENTION

One of the first operations in the manufacture of fabrics in a textile mill is a process known as "wraping." Wraping involves unwinding threads from their individual spindles and collecting them onto a large drum by rewinding them in side by side relationship onto the drum. The apparatus that performs this function is known as a "wraper."

The wraping operation should be performed as quickly as possible, with all threads wrapped at even, or substantially even tension, and without any interruptions, for example due to thread breakage ("broken end"). In some cases, variations of 10% in tension from thread to thread are considered unacceptable. In practice, however, fluctuations in tension occur and measures must be taken to keep the fluctuations within tolerance, for example, adjustment of the thread tensioning device associated with the wraper. Additionally, thread breakages must be detected as soon as possible so that the wraper can be stopped before the broken end of the thread is lost on the drum. Failure to meet these requirements can result in quality control problems and costly down time.

In the prior art, mechanical devices are commonly employed to detect thread breakage. The most commonly employed device comprises a cantilevered arm whose free end urges against the thread. The arm is coupled to an electrical contact that opens (or breaks) when the thread breaks. A significant disadvantage of this device is that it is incapable of providing indications of tension fluctuations that occur during operation of the wraper. Another disadvantage is the unreliability of a mechanical contact due to corrosion, dirt and thread filaments.

U.S. Pat. No. 4,883,531 describes a thread friction measurement device that employs u pair of strain gauges coupled to a pair of guide rollers over which the thread rides. It is said that the strain gauges provide electrical outputs corresponding to the tension in the thread before and after turning around the roller guides. However, devices of this type have numerous drawbacks which limit their practical use as a thread tension and breakage sensor. First, the imposition of the guide rollers in the thread path adds friction and hence increases the thread tension beyond that set by the tensioning device. The friction imposed by the rollers can be great enough to itself cause the thread to break, especially if the thread is of thin gauge. Second, the thread weaves an elaborate path through the device and hence the thread is difficult to reweave through the device after a breakage has occurred. Third, plural sensors, in this case two strain gauges, are required to obtain a measurement of thread tension and thus these types of devices are relatively expensive to manufacture. Fourth, due to the complexity of the device, it is unlikely that it can reliably provide the sensitivity required for tension detection, or that it can reliably react to a broken thread with the requisite speed. Fifth, strain gauges are static devices that provide outputs irrespective of their loading status, and circuitry such as null and span adjustments must be provided for calibration. Drift can occur over short periods of time, and/or as a result of temperature and/or humidity changes, thus causing erroneous outputs.

It is therefore desirable to provide a thread sensor for use with a tensioning device associated with the wraper which is simple, reliable, relatively inexpensive to manufacture, and which does not substantially alter the thread path and does no introduce appreciable friction and hence tension to the thread. It is also desirable that the thread sensor be capable of sensing as little as 10% fluctuation in thread tension and react very quickly to thread breakage. The present invention achieves these goals.

SUMMARY OF THE INVENTION

According to the invention, a sensor for use with a continuous material, such as but not limited to thread, comprises deflectable means for contacting material woven through the sensor and being deflectable by the material, and piezoelectric film means operatively coupled to the deflectable means for providing signals in response to deflections of the deflectable means. The signals thus provided are indicative of a condition of the material. According to the invention, the material travels in a substantially straight path through the sensor and the deflectable means is deflectable by an amount corresponding to material tension. The signals provided by the piezoelectric film means have an instantaneous magnitude indicative of an instantaneous magnitude of material tension and an instantaneous frequency indicative of an instantaneous material speed. Thus, the sensor may be employed to monitor both material tension and material speed, as well as the occurrence of broken material. Various embodiments of a material sensor employing deflectable means and piezoelectric film means for providing such signals are described.

BRIEF DESCRIPTION OF THE DRAWINGS

FIG. 1 is a side plan view of one embodiment of a material sensor in accordance with the present invention.

FIG. 4 is a sectional view of another embodiment of a material sensor according to the present invention.

DETAILED DESCRIPTION OF THE INVENTION

Figure 2:
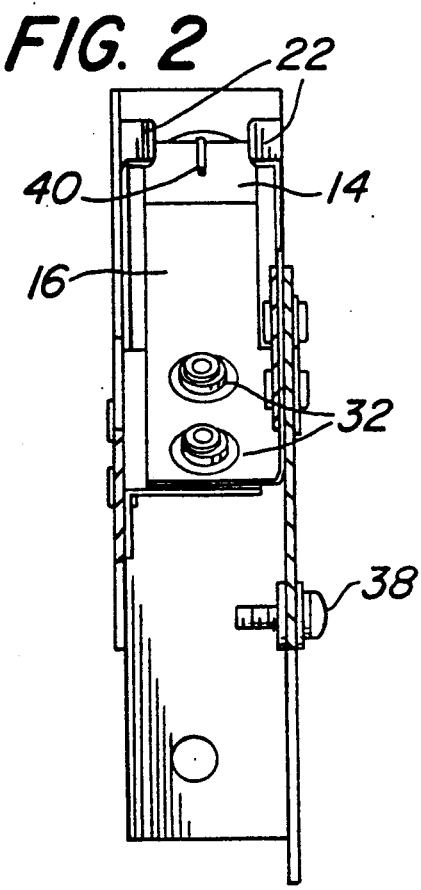
FIG. 2 is a top plan view of the sensor of FIG. 1.

Referring now to the drawings, wherein like numerals represent like elements, there is illustrated in FIGS. 1, 4, 5, 6, 7, and 10 various embodiments of a material sensor according to the present invention. While the particular material described herein is thread, it should be understood that the invention is in no way limited to use as a thread sensor. Thus, for purposes of convenience, the invention is described as a thread sensor, but it should be appreciated that the invention has application to nearly any type of continuous material that must be monitored for tension and breakage.

The details of each embodiment of the invention set forth in the drawings differ from each other in one respect or another, but each embodiment incorporates the following features central to the practice of the instant invention:

a) deflectable means (14, 14', 14", 14''') for contacting thread woven through the sensor and being deflectable by the thread; and, b) piezoelectric film means (16, 16', 16", 16''') operatively coupled to the deflectable means for providing signals in response to deflections of the deflectable means, wherein the signal is indicative of a condition of the thread, such as tension, speed and/or broken end. Moreover, in each embodiment, the thread travels in a substantially straight path through the sensor so that weaving of the thread therethrough is a simple matter.

Preferably, in the practice of the invention, the piezoelectric film means 16, 16', 16", 16''' is a poled, polymeric piezomaterial such as poled polyvinylidene fluoride (PVDF); a poled copolymer of vinylidene fluoride (VDF), such as a copolymer of VDF with at least one of trifluoroethylene (TrFE), tetrafluoroetheylene, hexafluoroethylene, or vinylidene chloride; a poled polymer of polyvinyl chloride or, a poled polymer of a acrylonitrile. One suitable polyvinylidene fluoride film is manufactured under the registered trademark KYNAR ® by Atochem North America, Philadelphia, Penna., although other polymeric piezofilms can be utilized without departure from the true scope of the invention. The other above mentioned films that can be employed in the practice of the invention are also commercially available. More detailed information relating to these particular piezofilms can be found in the "KYNAR ® Piezo Film Product Summary and Price List" (1988) available from Atochem North America of Philadelphia, Penna. Additional information relating to the structure, properties, application and fabrication of KYNAR ® piezo film can be found in the "KYNAR ® Piezo Film Technical Manual" (1987) also available from Atochem North America. Both of these publications are incorporated herein by reference.

Hereafter, except as noted, it should be understood that the aforementioned materials may be employed for the piezoelectric films described in connection with the various embodiments.

The details of the various embodiments of the present invention will now be described.

Figure 3:
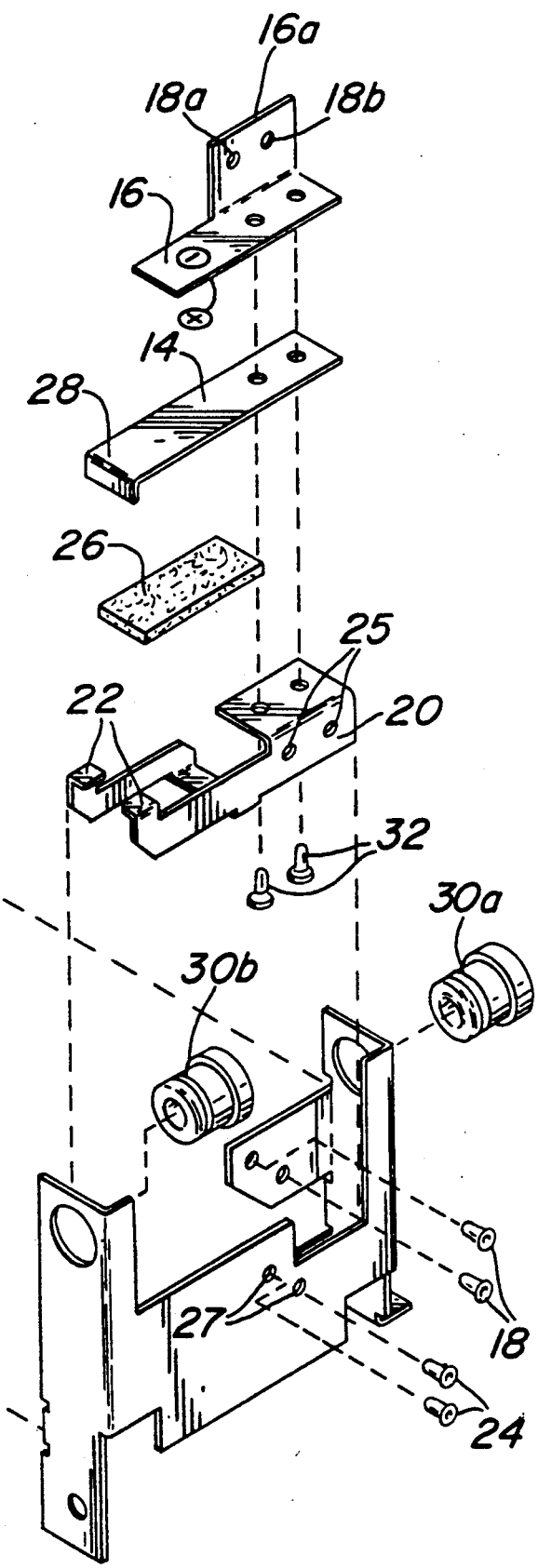
FIG. 3 is an exploded view of the sensor of FIG. 1.

FIGS. 1, 2 and 3 illustrate a first embodiment of a thread sensor according to the present invention. A thread sensor 10 comprises a body 12 having a pair of eyelets 30a, 30b defining inlets and outlets, respectively, of the sensor 10 for passage of thread 40 therethrough. The eyelets 30a, 30b therefore define guide means for passage of the thread 40 through the body 12 of the sensor 10. Disposed within the body 12 is a cantilever beam 14 (deflectable means) fixed at one end to the body 12 by means to be described hereafter. The beam 14 may be constructed of spring steel, such as SAE 1095 spring steel, blue tempered, 0.004 inch thick. In one embodiment of the invention, the dimensions of the beam 14 are 1.425 inches (length) by 0.312 inch (width). The beam 14 is biased so that the free end 28 urges against thread 40 passing through the eyelets 30a, 30b. As will be appreciated, the eyelets 30a, 30b define a substantially straight path for passage of thread 40, and the beam 14 will deflect more or less in response to changes in thread tension. The beam will also vibrate from the mere movement of thread over the free end 28. As shown, the free end 28 of the beam 14 may have a portion that is bent downwardly to provide a smooth edge for contacting the thread 40.

Figure 10A:
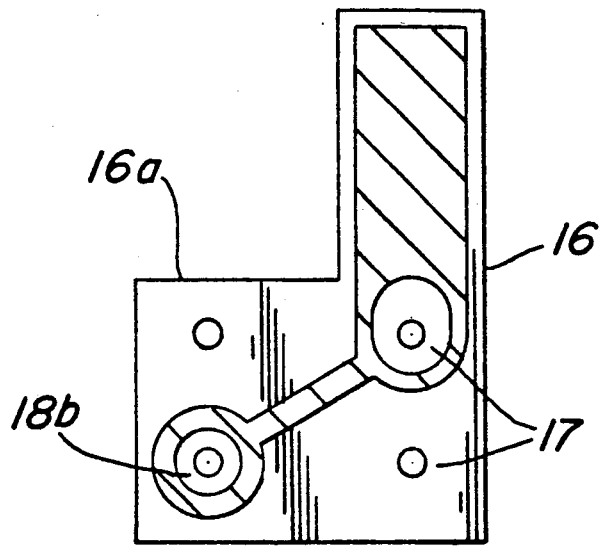
FIGS. 10A and 10B illustrates an exemplary structure for the piezo film employed in the disclosed implementation of the invention.
Figure 10B:
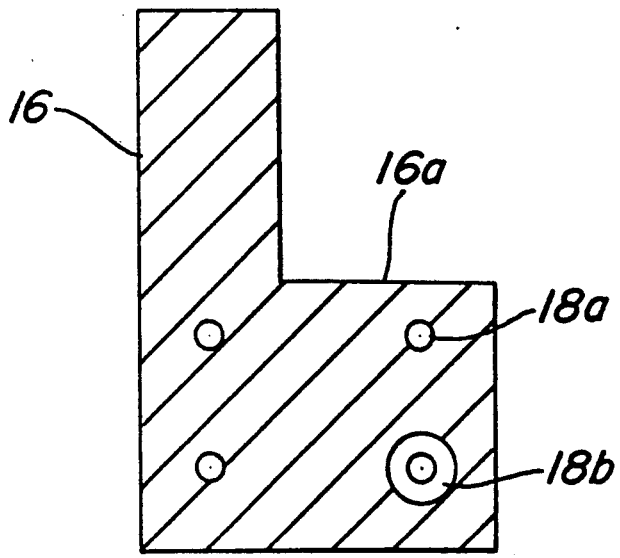

A strip of piezoelectric film 16 is affixed to the upper surface of the beam 14 by any suitable means. In the embodiment of the invention illustrated in FIG. 2, the strip of piezo film 16 is affixed to the beam 14 by means of adhesive. Preferably, the positive side of film 16 is layered between the negative side of the film 16, which is grounded, and the upper surface of the beam 14, which is also grounded. In other words, the upper surface of the film 16 is its negative side and the positive side of the film faces toward the upper surface of the beam 14. The adhesive also electrically insulates the positive side of the film 16 from the upper surface of the beam 14. The film 16 is thereby effectively shielded. FIGS. 10A and 10B illustrate one embodiment of the piezo film 16, with FIG. 10A depicting the positive side and FIG. 10B depicting the negative side. As shown, the entire negative side is metallized, while only a portion of the positive side is metallized. Metallization of film 16 is described in more detail below. The metallization pattern of the positive side (as well as hole clearances) serve to ensure &:hat proper electrical connections are made from the piezo film to circuitry, as will become evident hereinafter.

Fasteners 32 also affix the distal end of the piezo film 16 to the beam 14, and further serve to fasten the fixed end of the beam 14 to a bracket 20, which in turn is affixed to the body 12 by means of fasteners 24 extending through holes 25, 27. It will be appreciated from FIGS. 1 and 3 that the holes 25 in the bracket. 20 will align with holes 27 in the body 12, so that fasteners 24 may be placed therethrough, when the bracket 20 is tilted as shown in FIG. 1.

Fasteners 32 are electrically conductive. It will therefore be appreciated from FIGS. 10A and 10B that the fasteners 32 electrically connect the negative side of the film 16 to the beam 28 and to the bracket 20, which are grounded. As will be apparent from FIGS. 3 and 10A, the fasteners 32 will not short &:he positive side of film 16 to ground due to the absence of metallization in areas 17 and hole clearances.

In one preferred practice of the embodiment illustrated in FIGS. 1, 2 and 3, the length of the strip of piezo film 16 is about 0.5 inch and the width thereof is about 0.232 inch. In this embodiment, the thickness of the piezo film 16 is 28 um (micrometers). Preferably, the piezo film 16 is plasma etched, poled KYNAR ® and is coated with a layer of metallization by any well known technique such as screen printing silver ink thereon. In one presently preferred embodiment, the metallization has a surface resistivity of less than 1.5 ohms per square inch.

The strip of piezo film 16 may be provided with an integral, upwardly extending tab 16a having holes 18a, 18b. The metallization around one of the holes 18b is such that an electrical connection will be established between the positive side of film 16 and a plated through hole 18c of a circuit board 36 by means of an electrically conductive fastener 18 without shorting to ground or the negative side of the film 16. See FIGS. 1, 10A and 10B. Similarly, the metallization around the other hole 18a is such that an electrical connection will be established between the negative side of film 16 and another plated through hole 18c (defining ground) of the circuit board 36 by means of another electrically conductive fastener 18 without shorting to the positive side. The circuit board 36 contains circuitry for processing signals provided by the piezo film 16, as described in more detail below.

The fasteners 18, 24 and 32 may be conventional pop rivets.

In this, and all other embodiments of the invention, when the piezo film 16 is a material such as polyvinylidene fluoride requiring mechanical orientation to enhance its piezoelectric action, the stretch direction of the piezo film 16 is preferably in the longitudinal direction of the strip 16. In other words, the length of the strip 16 is also the stretch direction of the film 16.

It will be appreciated that deflections of the beam 14 will cause compression or tension of piezo film strip 16 (depending upon the direction of deflection) which in turn will cause the film 16 to produce a corresponding electrical signal. It will also be appreciated that the magnitude of the deflection of the beam 14 will result in an electrical signal having a corresponding magnitude. In other words, the greater the deflection, the greater the magnitude of the resulting electrical signal. Thus, as fluctuations in thread tension occur, the beam 14 will deflect in one direction or the other, thus resulting in corresponding electrical signals The greater the magnitude of fluctuations in thread tension, the greater the magnitude of the resulting electrical signals. Moreover, during normal operation, when even minor variations in thread tension occur, the beam 14 will undergo minor deflections or vibrate as a result of thread motion, so that the resulting electrical signals will oscillate. It will be appreciated that the frequency of oscillation of the signal will directly correspond to the speed of thread 40 passing through the body 12 and over the free end 28 of the beam 14. Thus, the signal has an instantaneous magnitude indicative of an instantaneous magnitude of thread tension and an instantaneous frequency indicative of an instantaneous thread speed. Increases in thread speed may also result in increases in signal magnitude.

Except as may be noted, all of the foregoing is equally applicable to all embodiments of the invention described herein.

The sensor thus far described has been shown to reliably provide signals indicative of thread tension and speed. However, it is also desirable that the sensor have the capability of rapidly detecting a thread breakage (broken end) and providing an output signal indicative of this event. While the sensor thus far described could be employed or detecting thread breakages (e.g., by monitoring the signal and observing whether it decays to a baseline, such as zero volts), the sensor of FIGS. 1, 2 and 3 may be provided with means for more rapidly and reliably detecting a broken thread and providing a corresponding output signal. Accordingly, the bracket 20 of the thread sensor of FIGS. 1, 2 and 3 may be provided with a pair of tabs 22 projecting over the free end 28 of the beam 14 so as to define a stop for the free end of the beam 14 in the event of a thread breakage. The stop defined by the tabs 22 (as well as other embodiments of stops to be described herein) have been found to provide the following effect. The effect can best be understood by reference to FIG. 9, as well as to FIG. 1. Beam 14 is normally deflected downwardly by action of the thread 40 passing over the free end 28 thereof. During this time, the beam 14 deflects more or less as a result of normal fluctuation in the thread 40. Thus, during this time, a waveform such as waveform 100 (FIG. 9) might be expected (the waveform of FIG. 9 has been buffered by a circuit of the type to be described hereinafter). When a thread break occurs, the thread tension is relieved and beam 14 undergoes a large deflection as it returns toward the tabs 22. The large beam deflection towards the tabs 22 creates a drop in tension on &:he film 16, which in turn creates a large signal 104. After striking the tabs, the beam begins to undergo transient vibrations, causing electrical transients 110, and this portion of the signal is superimposed on the discharge of the signal 104. The advantage of the signal being superimposed is that the transient signal is moved away from the zero output level 106, leaving little or no signal above zero after a break has occurred. Thus, a broken thread can be detected substantially immediately upon its occurrence by either looking for the occurrence of the large signal 104 or looking for the lack of signal above zero level 106. Thus, the RC time constant (described in more detail below) is preferably chosen to prolong the time of discharge of the charge developed by the film when the thread breaks causing the beam 20 to deflect back to the tabs 22. This prolongation serves as a means of eliminating signals of polarity and amplitude that would indicate the presence of tension, thus serving as a means of quickly indicating the lack of thread tension and the occurrence of a thread break.

Figure 8:
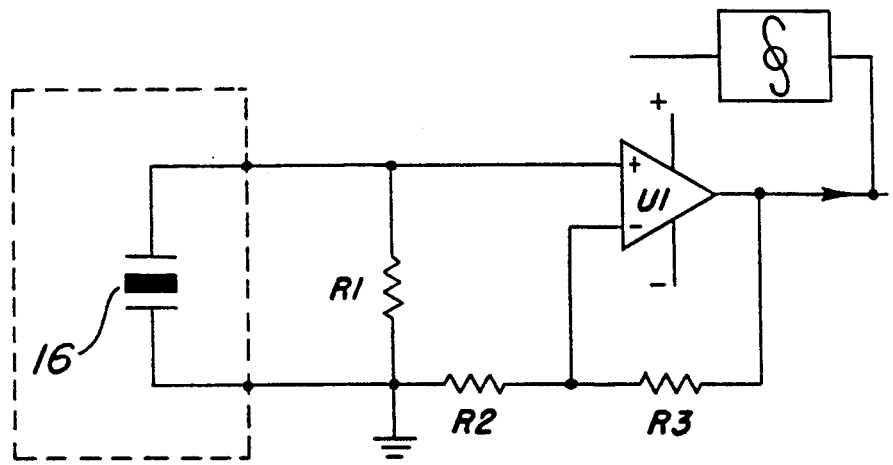
FIG. 8 is a simplified schematic diagram of exemplary electronic circuitry for conditioning and monitoring signals provided by sensors of the present invention.
Figure 9:
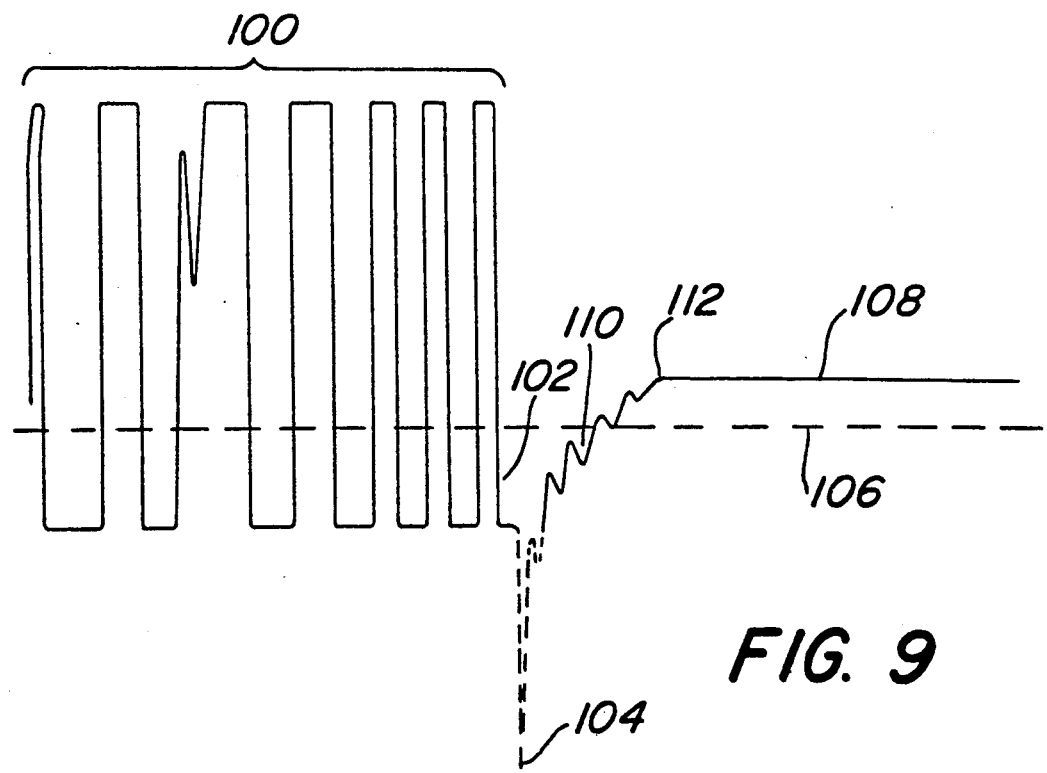
FIG. 9 illustrates an exemplary signal provided by the circuitry of FIG. 8 when coupled to a sensor of the present invention.

In FIG. 9, the negative going portion 104 is shown in dotted lines to illustrate that it cannot exceed the magnitude of the supply voltage to the amplifier U1 (FIG. 8). However, those skilled in the art will appreciate that the amplifier circuitry can be configured to recover the portion 104 so that its occurrence can be detected as above described.

The tabs 22 reduce the time it takes for the transient signal to decay by converting the energy of the vibrating beam into other forms of energy upon impact of the beam against the tab surfaces. Reducing the time of decay of the transient signal allows for a quicker detection of thread break by looking for the lack of signal. If desired, a strip of foam 26 may be affixed to the underside of the beam 14 for dampening of the transient vibration of the beam 14 upon thread breakage. However, use of the foam strip 26 is not necessary to practice of the present invention.

Circuit means may be provided for processing signals provided by the piezo film strip 16, e.g., for buffering the signals and/or providing drive capability. Conveniently, such circuitry may be provided on a circuit board 36 that may be affixed to the body 12 of the sensor 10 by suitable means such as fastening means 38. The circuit board 36 may have an edge 34 for mating with an edge connector of any desired type.

FIG. 8 illustrates one presently preferred form of circuitry for use in connection with the present invention. As illustrated, the output of the piezo film 16 is coupled in parallel to a resistor R1, then to an input of an amplifier U1 having a desired gain selected by adjusting the values of resistors R2 and R3. The circuit of FIG. 8 performs two primary functions. The first is to buffer and provide gain to the signal provided by the piezo film strip 16. The second is as follows. It has been found that the piezo film 16 has an intrinsic capacitance C which, of course, will vary depending upon the particular material chosen for piezo film 16, as well as its size and thickness. The particular strip 16 herein described above has been found to have an intrinsic capacitance of about 0.39 nanofarads. There is therefore a time constant associated with the decay of signals provided by the piezo film strip 16. It has been found that this time constant can be adjusted by proper selection of the resistor R1 in the circuit of FIG. 8. Since after thread break it is desirable to have no signals of opposite polarity to that of signal 104, selection of the values R and C (to the extent that the value of C can be altered) can alter the amount of transient signal that crosses the zero level in the opposite polarity aforementioned. In other words, a large time constant on the discharge of signal 104 allows time for the transient signal to decay such that as the discharge of signal 104 nears zero, the amplitude of the transient signal is nearly zero and, hence, does not cross into the opposite polarity. Emperical results have shown that, for a piezo film strip 16 having the stated intrinsic capacitance, a value for resistor R1 in the range of 1 megaohm to 10 megaohm has produced satisfactory results. Stated otherwise, selecting the values of R and C (to the extent that the value of C can be altered) for a time constant in the range of about 0.39 milliseconds to 3.9 milliseconds has been found to provide satisfactory results. The waveform of FIG. 9 was obtained when a value of 10 megaohm was employed for resistor R1 (time constant equal 3.9 milliseconds). More particularly, referring to FIG. 9, dampening of the transient 104 to the substantially zero DC level 108 (i.e., the time between 102 and 112) can be made as low as 30-80 milliseconds, with a 50 millisecond average, when the time constant is selected as above described.

The circuit of FIG. 8 may be employed with all embodiments of the invention disclosed herein, and the principles discussed in connection with FIG. 8 are equally applicable thereto. If desired, the circuitry of FIG. 8 may be provided with integrating means for providing a DC signal having a magnitude indicative of average thread tension. The integrating means may be embodied in any well known form, such as an integrating operational amplifier.

Figure 6:
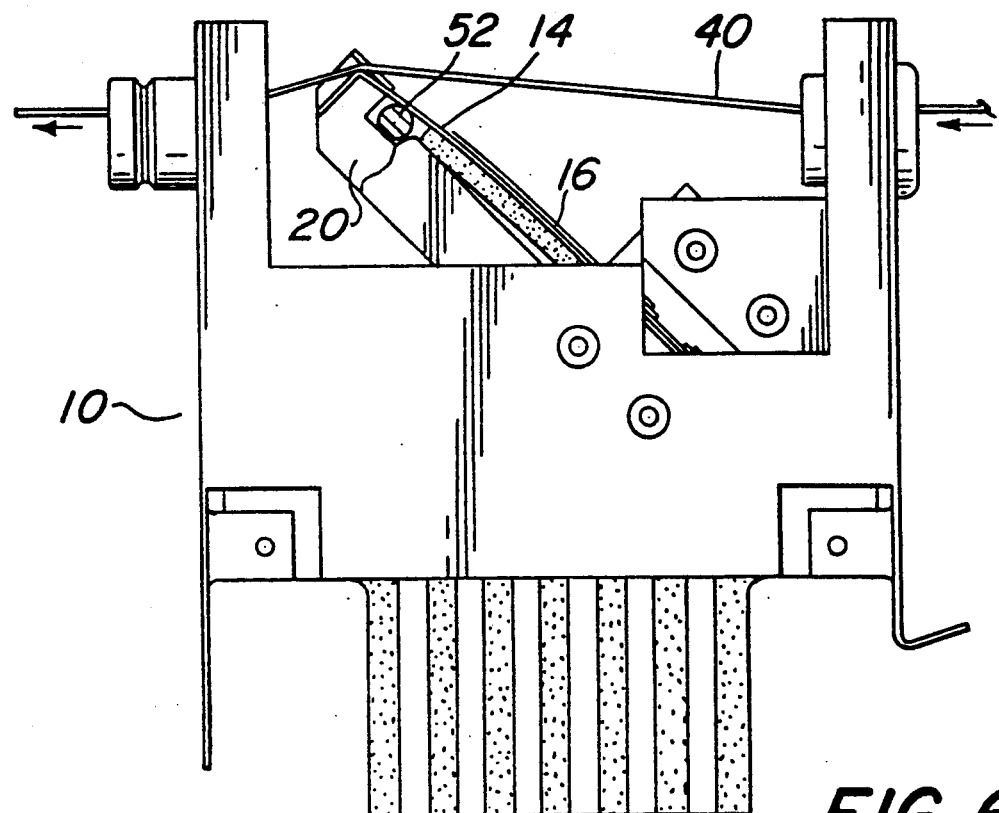
FIG. 6 is a side plan view of modified version of the sensor of FIG. 1.

FIG. 6 illustrates a modification to the sensor embodiment of FIGS. 1, 2 and 3. The sensor of FIG. 6 is identical to the sensor of FIGS. 1, 2 and 3, except that a transverse rod 52 is disposed between the underside of the beam 14 and the beam bracket 20. It has been found that when the transverse rod 52 is employed as shown the sensor becomes more responsive to normal forces applied to the beam 14 by the thread 40. Observation has shown that the rod 52 causes the beam to bend intermediate the rod 52 and its fixed end, thus applying tension to the piezo film 16, which in turn provides corresponding output signals.

Figure 5:
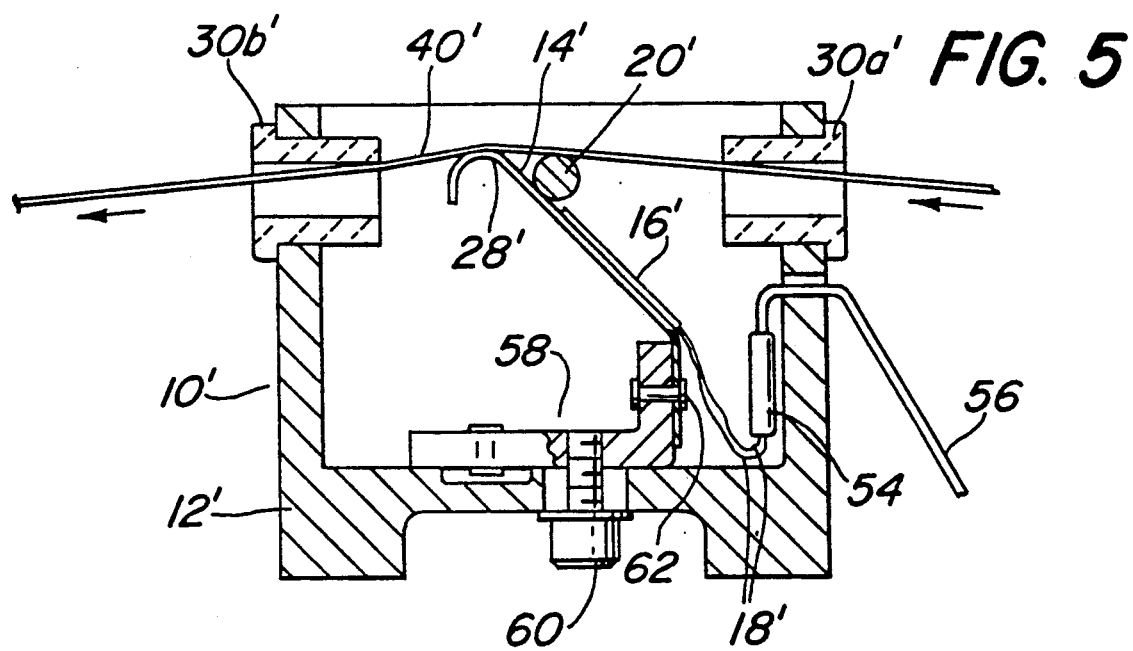
FIG. 5 is a sectional view of yet another embodiment of a material sensor according to the present invention.

FIG. 5 illustrates another embodiment of a thread sensor 10' according to the present invention. The principles discussed in connection with the embodiments of FIGS. 1, 2 and 3 are applicable to FIG. 5, except as noted herein. As before, the thread sensor 10' comprises a body 12' having a pair of eyelets 30a', 30b' defining inlets and outlets, respectively, of the thread sensor 10'. Again, as before, a cantilever beam 14' has a strip of piezoelectric film 16' affixed thereto by any suitable means, e.g., by adhesive. The characteristics of the piezo film strip 16' may be as described above. A free end 28' of the cantilever beam 14' is biased to urge against thread 40' passing through the body 12' so to deflect in response to fluctuations in thread tension and vibrate in response to thread movement. The principal differences between the embodiment of FIG. 5 and the embodiment of FIGS. 1, 2 and 3 are as follows. First, a rod 20' disposed adjacent the upper side of the beam 14' extends transversely of the body 12' and defines a stop for upward deflections of the beam 14'. Second, the end of the beam 14' opposite the free end 28' (i.e., the fixed end) is affixed to an adjustable bracket 58 by fastening means 62. The bracket 58 is laterally adjustable by means of screw 60. Loosening of the screw 60 will permit the bracket 58 to be moved to the left or right, thereby altering the contact point of the free end 28' against the stop 20'. It will be appreciated that altering the contact point in this manner will cause the free end 28' to be biased upwardly or downwardly more or less when the beam 14' is in its rest position. Thus, adjustment of the bracket 58 adjusts a preload condition of the beam 14'.

Signals are produced by the piezo film strip 16' as before. Signals are conducted to circuitry (such as that shown in FIG. 8) by means of electrical conductors 18' which are coupled to, e.g., a shielded cable 56, at solder joint 54. As before, the circuit may be disposed on a circuit board affixed to the body 12', if desired.

FIG. 4 illustrates yet a further embodiment of a thread sensor 10" according to the present invention. Again, the thread sensor 10" comprises a body 12" having a cantilever beam 14" with a strip of piezoelectric film 16" affixed thereto, e.g., by adhesive means. Eyelets 30a", 30b" define inlets and outlets for passage of thread 40" through the body 12". As in the case of the embodiments of FIGS. 1, 2, 3 and 5, the eyelets 30a", 30b" define a substantially straight path for travel of the thread through the sensor 10". While the structure of sensor 10" of FIG. 4 is somewhat different from the embodiments of FIGS. 1, 2, 3 and 5, its operation is substantially the same. The cantilever beam 14" (deflectable means) is sandwiched between a pair of aluminum plates 46, 48 so as to define the fixed end thereof. The free end of the beam 14" has an eyelet (guide means) 42 disposed thereon. The aluminum plate 46 extends along a substantial portion of the beam 14" so as to define a stop for deflections of the beam 14".

Disposed on the distal end of the aluminum plate 46 is another eyelet (guide means) 44 in substantial alignment with the eyelet 42. Importantly, the eyelets 30a", 30b" are arranged to cause thread 40" passing through to frictionally engage the eyelet 42 disposed on the free end of the beam 14", as shown. It will be appreciated the frictional engagement of thread 40" against the interior periphery of eyelet 42 will cause beam 14" to vibrate when thread passe therethrough and to deflect in response to changes in thread tension. The strip of piezo film 16" may have the characteristics hereinbefore described. As before, the piezo film 16" will produce signals in response to vibrations and deflections of the beam 14". Electrical conductors 18" may be employed to carry the signals to a circuit of the type of FIG. 8, if desired.

Preferably, the eyelets 30a''', 30b''' are arranged so as to keep the thread 40'' close to the beam's end such that the incoming and exiting angle of the thread 40'' has little effect on output. It will be appreciated that, as thread tension increases, the beam will be displaced further and the amplitude of the signal produced by the piezo film 16'' will increase. When tension drops to zero, for example, when the thread breaks, the beam 14'' will rapidly move back to its position (against aluminum plate 46), thus dampening the output signal quickly, again reducing the settling time within 30–80 milliseconds and preferably to within 50 milliseconds.

Figure 7:
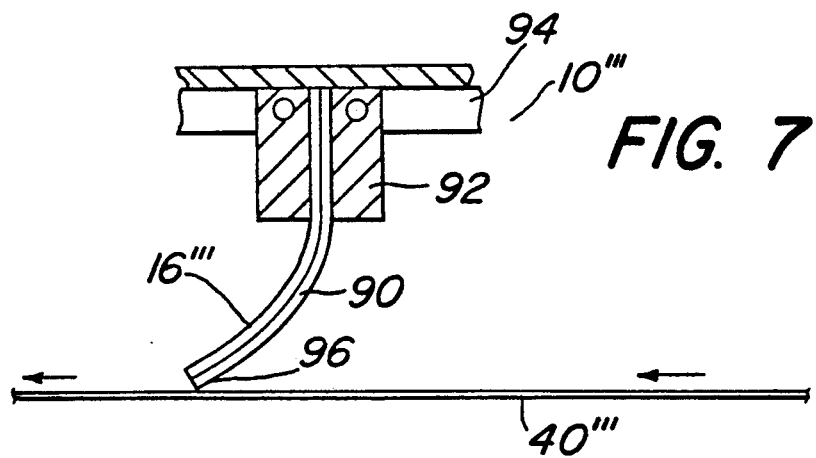
FIG. 7 illustrates yet another embodiment of a material sensor according to the present invention.

FIG. 7 illustrates a low cost embodiment of a thread sensor 10'''' according to the present invention. According to the embodiment of FIG. 7, the thread sensor 10'''' comprises a strip of piezoelectric film 16'''' laminated with an abrasion resistant material 90. The piezo film 16'''' and the lamination 90 define both the piezoelectric film means and deflectable means hereinbefore described. The piezoelectric film 16'''' may have the characteristics described above in connection with the other embodiments. The abrasion resistant material 90 is preferably plastic, such as polytetraflouroethylene film or Teflon ®. As shown, one end of the laminated piezo film 16'''', 90 is fixed to a clamp 92, which in turn is fixed to a bracket 94 so as to define a cantilever beam. The free end 96 of the cantilever beam contacts thread 40'''', which again travels in a substantially straight path. As the thread travels, the laminated piezo film 16'''', 90 deflects more or less with normal fluctuations in thread tension of thread passing thereby. When the thread breaks, the laminated piezo film 16'''', 90 will return to its original rest position. Thus, the piezoelectric film 16'''' will provide signals in the presence of passing thread, but no signals after the occurrence of a thread break.

As in the case of the embodiments of FIGS. 1–6, when the piezo film 16'''' employed in the embodiment of FIG. 7 requires mechanical orientation, it preferably has a stretch direction that is in the longitudinal direction of the strip 16'''' and is constructed of one of the polymers hereinbefore described.

The invention thus described provides a voltage output that varies in amplitude and frequency with the thread's tension and speed. This signal may be provided as a feedback signal to a thread tensioning device so that the device may automatically increase or decrease the thread's tension as required. In the event of a broken thread, the invention rapidly provides an indication of such event so that the thread tensioning device may automatically shut down before the thread's end is lost on the wraper's drum.

Many changes, modifications, variations and other uses and applications of the subject invention will become apparent to those skilled in the art after considering this specification and accompanying drawings which disclose preferred embodiments thereof. All such changes, modifications, variations and other uses of applications do not depart from the spirit and scope of the invention are deemed to be covered by the invention which is limited only by the claims which follow.

What is claimed is:

1. Material sensor comprising:
   a) deflectable means for contacting material woven through the sensor and being deflectable by the material;
   b) piezoelectric film means operatively coupled to the deflectable means for providing signals in response to deflections of the deflectable means, the signal being indicative of a condition of the material, wherein the deflectable means undergoes rapid and sudden deflection upon the occurrence of a broken material and the piezoelectric films develops charge thereon as a result of said rapid and sudden deflection; and
   c) circuit means coupled to the piezoelectric film means, and wherein the piezoelectric film means has an intrinsic capacitance C, and the circuit means comprises a resistor R coupled in RC relationship with the piezoelectric film means to define a discharge path having an RC time constant, the charge discharging through the discharge path, the RC time constant being selected to substantially minimize any substantial signal of opposite polarity to the polarity of the developed charge.

2. Material sensor according to claim 1 further comprising means defining a substantially straight material path through the sensor.

3. Material sensor according to claim 1 wherein the deflectable means is deflectable by an amount corresponding to material tension.

4. Material sensor according to claim 3 wherein the signal has an instantaneous magnitude indicative of an instantaneous magnitude of material tension and an instantaneous frequency indicative of an instantaneous material speed.

5. Material sensor according to claim 1 wherein the condition is material tension.

6. Material sensor according to claim 1 wherein the condition is whether the material has broken.

7. Material sensor according to claim 1 further comprising circuit means operatively coupled to the piezoelectric film means for providing a DC signal having a magnitude indicative of average material tension.

8. Material sensor according to claim 7 wherein the circuit is an integrating circuit.

9. Material sensor according to claim 1 Wherein the piezoelectric film means is one of: polyvinylidene fluoride; a copolymer of vinylidene fluoride a copolymer comprising vinylidene fluoride and at least one of trifluoroethylene, tetrafluoroethylene, hexafluoroethylene, and vinylidene chloride; a polymer of polyvinylchloride; or, a polymer of acrylonitrile.

10. Material sensor according to claim 1 wherein the piezoelectric film means is a generally longitudinal strip of piezoelectric film having a machine stretch direction in the longitudinal direction of the strip.

11. Material sensor according to claim 1 wherein the deflectable means comprises a cantilevered beam biased so that a free end thereof urges against the material.

12. Material sensor according to claim 11 wherein the cantilevered beam comprises a strip of spring steel and the piezoelectric film means is affixed to the spring steel.

13. A material sensor comprising:
   a) deflectable means for contacting material woven through the sensor and being deflectable by the material, wherein the deflectable means comprises a cantilevered beam biased so that a free end thereof urges against the material;
   b) piezoelectric film means operatively coupled to the deflectable means for providing signals in response to deflections of the deflectable means, the signal being indicative of a condition of the material; and c) a beam bracket fixed to a body of the sensor and having a pair of tabs projecting over a portion of the beam so as to define a stop for the free end of the beam.

14. Material sensor according to claim 11 further comprising a strip of foam affixed to an underside of the beam for dampening any tendency of the beam to vibrate.

15. Material sensor according to claim 11 further comprising a pair of guides affixed to portions of a body of the sensor defining inlet and outlet ends of the sensor, the guides being juxtaposed to direct the material over the free end of the beam.

16. Material sensor according to claim 13 further comprising a rod disposed between an underside of the beam and the beam bracket, material tension urging the beam against the rod and causing the beam to bend intermediate the rod and a fixed end thereof, the sensor thereby being responsive to normal forces applied to the beam by the material, the signals being indicative of the applied normal forces.

17. Material sensor according to claim 12 further comprising a rod disposed between an upper side of the beam and the material and defining a stop for the free end of the beam.

18. A material sensor, comprising:
a) deflectable means for contacting material woven through the sensor and being deflectable by the material, wherein the deflectable means comprises a cantilevered beam biased so that a free end thereof urges against the material, wherein the cantilevered beam comprises a strip of spring steel;
b) piezoelectric film means operatively coupled to the deflectable means for providing signals in response to deflections of the deflectable means, the signal being indicative of a condition of the material, wherein the piezoelectric film means is affixed to the spring steel; and
c) a rod disposed between an upper side of the beam and the material and defining a stop of the free end of the beam, wherein a portion of the beam opposite the free end is fixed to a bracket, the bracket being adjustable to alter a contact point of the free end of the beam against the stop so as to adjust a preload condition of the beam.

19. Material sensor according to claim 9 wherein the circuit means is disposed on a circuit board affixed to a body of the sensor and the circuit board comprises an edge for mating with an edge connector.

20. Material sensor according to claim 1 wherein the deflectable means comprises a cantilevered beam having a material guide disposed on a free end thereof for material to pass therethrough, the piezoelectric film means being adhered to a surface of the beam, the beam vibrating when material passes through the guide.

21. Material sensor according to claim 20 wherein a portion of the beam opposite the free end is sandwiched between a pair of plates, one of the plates extending along a substantial portion of the beam and defining a stop for deflections of the beam.

22. Material sensor according to claim 21 further comprising a pair of additional guides disposed on inlet and outlet sides of the sensor, respectively, the additional guides being arranged to cause the material to frictionally engage the guide disposed on the beam.

23. Material sensor according to claim 1 wherein the deflectable means is an abrasion resistant material cantilevered with a free end contacting the material and the piezoelectric film means is laminated with the abrasion resistant material.

24. Material sensor according to claim 23 wherein the abrasion resistant material is a plastic material.

25. Material sensor according to claim 24 wherein the plastic material is polytetraflouroethylene.

26. Material sensor according to claim 9 wherein a substantial portion of the signal normally exhibits at least a first polarity as material travels through the sensor, but upon the occurrence of a material break, the beam rapidly deflects to a stop located in a body of the sensor and the signal substantially ceases to exhibit the first polarity, the substantial cessation of the first polarity being indicative of the occurrence of a material breakage.

27. Material sensor according to claim 26 wherein, substantially immediately upon the occurrence of a material breakage, the signal exhibits a transient of a second, opposite polarity.

28. Apparatus for providing an indication of material tension and material breakage comprising:
a) guide means defining a substantially straight path for material to pass through a body;
b) a cantilever beam disposed within the body and having a free end biased to urge against material passing through the body and being deflectable in response to changes in material tension;
c) a strip of piezoelectric polymer film affixed to the cantilever beam and providing electrical signals in response to deflections of the cantilever beam, wherein the beam undergoes rapid and sudden deflection upon the occurrence of a broken material and the polymer film develops charge thereon as a result;
d) circuit means for processing the signals provided by the film, wherein the piezoelectric film means has an intrinsic capacitance C, and the circuit means comprises a resistor R coupled in RC relationship with the piezoelectric film means to define a discharge path having an RC time constant, the charge discharging through the discharge path, the RC time constant being selected to substantially minimize any substantial signal of opposite polarity to the polarity of the developed charge; and
the circuit means providing an output having a magnitude indicative of material tension and that assumes a defined particular state in the absence of material tension, the defined state being indicative of a material breakage.

29. Apparatus according to claim 28 further comprising a stop disposed within the body, the cantilever beam urging against the top in the body in the absence of material tension.

30. Apparatus for providing an indication of material tension and material breakage comprising:
a) guide means defining a substantially straight path for material to pass through a body;
b) a cantilever beam disposed within the body and having a free end biased to urge against material passing through the body and being deflectable in response to changes in material tension;
c) a strip of piezoelectric polymer film affixed to the cantilever beam and providing electrical signals in response to defections of the cantilever beam;
d) circuit means for processing the signals provided by the film, the circuit means providing an output having a magnitude indicative of material tension and that assumes a defined particular state in the absence of material tension, the defined state being indicative of a material breakage;

e) a stop disposed within the body, the cantilever beam urging against the stop in the body in the absence of material tension, wherein the stop comprises a beam bracket fixed to the body and having a pair of tabs projecting over the free end of the cantilever beam.

31. Apparatus for providing an indication of material tension and material breakage comprising:
   a) guide means defining a substantially straight path for material to pass through a body;
   b) a cantilever beam disposed within the body and having a free end biased to urge against material passing through the body and being deflectable in response to changes in material tension;
   c) a strip of piezoelectric polymer film affixed to the cantilever beam and providing electrical signals in response to deflections of the cantilever beam;
   d) circuit means for processing the signals provided by the film, the circuit means providing an output having a magnitude indicative of material tension and that assumes a defined particular state in the absence of material tension, the defined state being indicative of a material breakage;
   e) a stop disposed within the body, the cantilever beam urging against the stop in the body in the absence of material tension, wherein the stop comprises a rod disposed between an upper side of the beam and the path, a portion of the beam opposite the free end being fixed to an adjustable bracket, the bracket being adjustable to alter a point of contact of the free end against the stop and alter a preload condition of the beam.

32. Apparatus according to claim 28 further comprising a rod disposed adjacent the underside of the beam, material tension urging the beam against the rod and causing the beam to bend intermediate the rod and a fixed end thereof, the piezoelectric film being responsive to normal forces applied to the beam by the material, the signals being indicative of the applied normal forces.

33. Apparatus according to claim 28 further comprising a strip of foam affixed to an underside of the beam for dampening any tendency of the beam to vibrate.

34. Apparatus according to claim 28 wherein the beam is spring steel.

35. Apparatus according to claim 28 wherein the circuit is disposed on a circuit board affixed to the body and the circuit board comprises an edge for mating with an edge connector.

36. Apparatus for providing an indication of material tension and material breakage comprising:
   a) first guide means defining a substantially straight path for material to pass through a body;
   b) a cantilever beam disposed within the body and having second guide means disposed on a free end thereof for material to pass therethrough, the first guide means being arranged to cause the material to fictionally engage the second guide means, the beam vibrating when material passes through the second guide means and deflecting in response to changes in material tension;
   c) a strip of piezoelectric polymer film affixed to the cantilever beam and providing electrical signals in response to vibrations and deflections of the cantilever beam, wherein the beam undergoes rapid and sudden deflection upon the occurrence of a broken material and the polymer film develops charge thereon as a result; and
   d) circuit means for processing the signals provided by the piezoelectric film, the circuit means providing outputs indicative of material tension and material breakage, wherein the piezoelectric film means has an intrinsic capacitance C, and the circuit means comprises a resistor R coupled in RC relationship with the piezoelectric film means to define a discharge path having an RC time constant, the charge discharging through the discharge path, the RC time constant being selected to substantially minimize any substantial signal of opposite polarity to the polarity of the developed charge.

37. Apparatus according to claim 36 wherein a portion of the beam opposite the free end is sandwiched between a pair of plates, one of the plates extending along a substantial portion of the beam and defining a stop for deflections of the beam.

38. Apparatus according to claim 36 wherein the beam is spring steel.

39. Apparatus according to claim 36 wherein the circuit is disposed on a circuit board affixed to the body and the circuit board comprises an edge for mating with an edge connector.

40. Apparatus for providing an indication of material breakage comprising a strip of piezoelectric polymer film laminated with a resilient abrasion resistance material and cantilevered with a free end adapted to contact passing material to be monitored for breakage and being deflectable in response to changes in material tension but returning to a rest position upon the occurrence of a material breakage, the piezoelectric film providing signals in the presence of passing material but not signals after the occurrence of a material break, wherein the piezoelectric film undergoes rapid and sudden deflection upon the occurrence of a broken material and develops charge thereon as a result wherein the piezoelectric film has an intrinsic capacitance C and circuit means for processing the signals provided by the film the circuit means comprising a resistor R coupled in RC relationship with the piezoelectric film to define a discharge path having an RC time constant, the charge discharging through the discharge path, the RC time constant being selected to substantially minimize any substantial signal of opposite polarity to the polarity of the developed charge.

41. Apparatus according to claim 40 wherein the abrasion resistant material is plastic.

42. Apparatus according to claim 40 wherein the abrasion resistant material is polytetrafluoroethylene.

* * * * *